(12) United States Patent
Mao et al.

(10) Patent No.: US 10,540,697 B2
(45) Date of Patent: Jan. 21, 2020

(54) METHOD AND SYSTEM FOR A STYLING PLATFORM

(71) Applicant: Perfect365 Technology Company Ltd., Hangzhou (CN)

(72) Inventors: Kaixuan Mao, Dublin, CA (US);
Chiachi Wei, San Jose, CA (US);
Che-Hao Chang, San Jose, CA (US);
Hui Deng, San Ramon, CA (US);
Wanjiang Wang, Hangzhou (CN)

(73) Assignee: PERFECT365 TECHNOLOGY COMPANY LTD., Hangzhou (CN)

( * ) Notice: Subject to any disclaimer, the term of this patent is extended or adjusted under 35 U.S.C. 154(b) by 265 days.

(21) Appl. No.: 15/631,954

(22) Filed: Jun. 23, 2017

(65) Prior Publication Data

US 2018/0374128 A1    Dec. 27, 2018

(51) Int. Cl.
| | | |
|---|---|---|
| *G06Q 30/02* | (2012.01) | |
| *H04N 5/232* | (2006.01) | |
| *A61B 5/00* | (2006.01) | |
| *A45D 44/00* | (2006.01) | |
| *G06Q 30/06* | (2012.01) | |

(52) U.S. Cl.
CPC ....... *G06Q 30/0281* (2013.01); *A45D 44/005* (2013.01); *A61B 5/44* (2013.01); *G06Q 30/0264* (2013.01); *G06Q 30/0282* (2013.01); *H04N 5/23206* (2013.01); *G06Q 30/0631* (2013.01)

(58) Field of Classification Search
CPC .......... G06Q 30/0281; G06Q 30/0264; G06Q 30/0282; G06Q 30/0631; A61B 5/44; A45D 44/005; H04N 5/23206
See application file for complete search history.

(56) References Cited

U.S. PATENT DOCUMENTS

| | | | |
|---|---|---|---|
| 7,643,659 B2 | 1/2010 | Cao et al. | |
| 7,751,599 B2 | 7/2010 | Chen et al. | |
| 8,295,557 B2 | 10/2012 | Wang et al. | |
| 8,693,768 B1 * | 4/2014 | LaForgia | A45D 44/005 222/1 |
| 8,913,839 B2 | 12/2014 | Ricanek, Jr. et al. | |
| 8,977,056 B2 | 3/2015 | Susanu et al. | |
| 10,052,026 B1 * | 8/2018 | Tran | G16H 50/30 |
| 2004/0110113 A1 * | 6/2004 | Huang | G09B 19/00 434/100 |
| 2010/0030578 A1 * | 2/2010 | Siddique | G06Q 10/0637 705/3 |

(Continued)

*Primary Examiner* — Blake J Rubin
(74) *Attorney, Agent, or Firm* — Nicholson De Vos Webster & Elliott LLP

(57) ABSTRACT

Embodiments of the invention include methods and systems for a styling platform. In one embodiment, a method is implemented in a beauty application of a mobile device. The method includes applying a styling feature to a facial image through the beauty application, the method further includes transmitting a message from a first user to a second user through the beauty application, the message containing a hyperlink to the facial image with the styling feature applied. The method further includes establishing a communication session within the beauty application between the first and second users responsive to receiving a reply from the second user, and exchanging information regarding the styling feature within the beauty application between the first and second users using the communication session.

20 Claims, 10 Drawing Sheets

(56) References Cited

U.S. PATENT DOCUMENTS

| | | | |
|---|---|---|---|
| 2010/0185064 A1* | 7/2010 | Bandic | A61B 5/0059 |
| | | | 600/306 |
| 2011/0052012 A1 | 3/2011 | Bambha et al. | |
| 2013/0021460 A1* | 1/2013 | Burdoucci | A45D 44/005 |
| | | | 348/77 |
| 2013/0060614 A1* | 3/2013 | Anikina | G06Q 10/10 |
| | | | 705/14.4 |
| 2013/0088513 A1 | 4/2013 | Deng | |
| 2013/0111337 A1 | 5/2013 | Deng et al. | |
| 2013/0215116 A1* | 8/2013 | Siddique | G06Q 30/0643 |
| | | | 345/420 |
| 2014/0279192 A1* | 9/2014 | Selby | G06Q 30/0631 |
| | | | 705/26.7 |
| 2014/0372236 A1* | 12/2014 | Sylvester | G07G 1/0009 |
| | | | 705/22 |
| 2015/0052008 A1* | 2/2015 | Campbell | G06Q 30/0633 |
| | | | 705/26.8 |
| 2015/0346936 A1* | 12/2015 | Rodan | G06F 19/3481 |
| | | | 715/745 |
| 2015/0365627 A1 | 12/2015 | Deng et al. | |
| 2015/0366328 A1* | 12/2015 | Tamura | A45D 44/00 |
| | | | 434/100 |
| 2016/0267403 A1* | 9/2016 | Hoffart | G06Q 10/02 |
| 2017/0024589 A1* | 1/2017 | Schumacher | G06F 3/0481 |
| 2017/0352092 A1* | 12/2017 | Mitchell | G06T 15/503 |
| 2018/0211308 A1* | 7/2018 | Cheeks | G06Q 30/0643 |
| 2018/0268572 A1* | 9/2018 | Nishi | G06T 7/73 |
| 2019/0019235 A1* | 1/2019 | Sprangers | G06Q 30/0631 |
| 2019/0034907 A1* | 1/2019 | Powers | G06Q 30/06 |
| 2019/0035163 A1* | 1/2019 | Skwarek | A45D 44/005 |

\* cited by examiner

FIG. 9

METHOD AND SYSTEM FOR A STYLING PLATFORM

TECHNICAL FIELD

Embodiments of the invention relate to an online platform for beauty artists.

BACKGROUND

Beauty artists traditionally work with consumers offline. A consumer may bring a facial or hair style for a beauty artist to apply, and once the beauty artist applies the style on the consumer's face or hair, the consumer gives feedback for the beauty artist to revise. The feedback happens as the beauty artist is applying the style or after the style is already applied. The beauty artist has to remove or revise the style that's physically on the consumer based on the feedback. Consumer may give more feedback until the consumer satisfies with the style. The process can be long, tedious, and costly for both beauty artist and consumer.

BRIEF DESCRIPTION OF THE DRAWINGS

The invention may best be understood by referring to the following description and accompanying drawings that illustrate embodiments of the invention. In the drawings:

FIG. 9 illustrates making a purchase through a styling platform per one embodiment of the invention.

DETAILED DESCRIPTION

Figure 1:
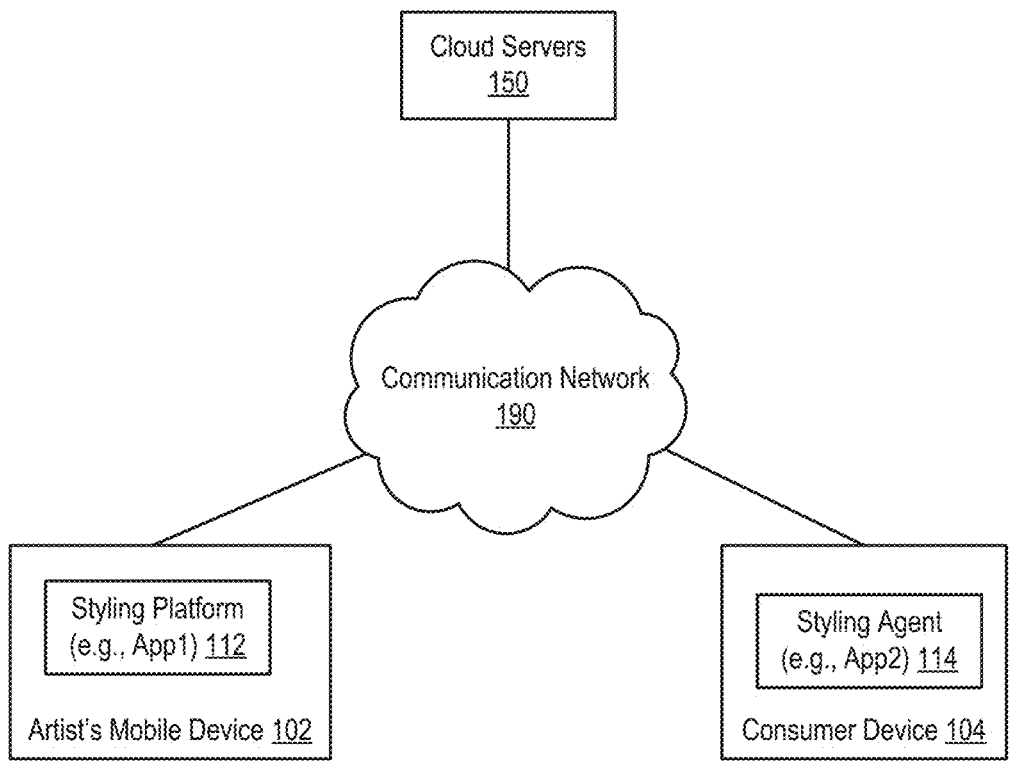
FIG. 1 illustrates the operating environment of a styling platform in a mobile device per one embodiment of the invention.

The following description describes methods and apparatus to implement a platform for a makeup artist. In the following description, numerous specific details such as logic implementations, opcodes, means to specify operands, resource partitioning/sharing/duplication implementations, types and interrelationships of system components, and logic partitioning/integration choices are set forth to provide a more thorough understanding of the present invention. One skilled in the art will appreciate, however, that the invention may be practiced without such specific details. In other instances, control structures, gate level circuits and full software instruction sequences have not been shown in detail in order not to obscure the invention. Those of ordinary skill in the art, with the included descriptions, will be able to implement proper functionality without undue experimentation.

Bracketed text and blocks with dashed borders (such as large dashes, small dashes, dot-dash, and dots) may be used to illustrate optional operations that add additional features to the embodiments of the invention. Such notation, however, should not be taken to mean that these are the only options or optional operations, and/or that blocks with solid borders are not optional in some embodiments of the invention.

Terms

References in the specification to "one embodiment," "an embodiment," "an example embodiment," and so forth, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following description and claims may use the terms "coupled" and "connected," along with their derivatives. These terms are not intended as synonyms for each other. "Coupled" is used to indicate that two or more elements, which may or may not be in direct physical or electrical contact with each other, co-operate or interact with each other. "Connected" is used to indicate the establishment of communication between two or more elements that are coupled with each other.

An electronic device stores and transmits (internally and/or with other electronic devices over a network) code (which is composed of software instructions and which is sometimes referred to as computer program code or a computer program) and/or data using machine-readable media (also called computer-readable media), such as machine-readable storage media (e.g., magnetic disks, optical disks, solid state drives, read only memory (ROM), flash memory devices, phase change memory) and machine-readable transmission media (also called a carrier) (e.g., electrical, optical, radio, acoustical or other form of propagated signals—such as carrier waves, infrared signals). Thus, an electronic device (e.g., a computer) includes hardware and software, such as a set of one or more processors (e.g., of which a processor is a microprocessor, controller, microcontroller, central processing unit, digital signal processor, application specific integrated circuit, field programmable gate array, other electronic circuitry, a combination of one or more of the preceding) coupled to one or more machine-readable storage media to store code for execution on the set of processors and/or to store data. For instance, an electronic device may include non-volatile memory containing the code since the non-volatile memory can persist code/data even when the electronic device is turned off (when power is removed). When the electronic device is turned on, that part of the code that is to be executed by the processor(s) of the electronic device is typically copied from the slower non-volatile memory into volatile memory (e.g., dynamic random-access memory (DRAM), static random-access memory (SRAM)) of the electronic device. Typical electronic devices also include a set of one or more physical network interface(s) (NI(s)) to establish network connections (to transmit and/or receive code and/or data using propagating signals) with other electronic devices. For example, the set of physical NIs (or the set of physical NI(s) in combination with the set of processors executing code) may perform any formatting, coding, or translating to allow the electronic device to send and receive data whether over a wired and/or a wireless connection. In some embodiments, a physical NI may comprise radio circuitry capable of (1) receiving data from other electronic devices over a wireless connection and/or (2) sending data out to other devices through a wireless connection. This radio circuitry may include transmitter(s), receiver(s), and/or transceiver(s) suitable for radiofrequency communication. The radio circuitry may convert digital data into a radio signal having the proper parameters (e.g., frequency, timing, channel, bandwidth, and so forth). The radio signal may then be transmitted through antennas to the appropriate recipient(s). In some embodiments, the set of physical NI(s) may comprise network interface controller(s) (NICs), also known as a network interface card, network adapter, or local area network (LAN) adapter. The NIC(s) may facilitate in connecting the electronic device to other electronic devices allowing them to communicate with wire through plugging in a cable to a physical port connected to a NIC. One or more parts of an embodiment of the invention may be implemented using different combinations of software, firmware, and/or hardware.

A mobile device is an electronic device that communicatively interconnects other electronic devices on the network and is often small enough to be held and operated in a human hand. A mobile device may be a tablet, a palm-top, a mobile phone, a smartphone, a phablet, a multimedia phones, a Voice Over Internet Protocol (VOIP) phone, a portable media player, a global positioning system (GPS) unit, a gaming system, a wearable device, or a laptop computer.

A mobile application (also referred to as mobile software application, mobile app, or simply app) is a software application designed to run on a mobile device. A mobile application runs directly on a mobile device (rather than through a web browser) once downloaded to the mobile device from an app store (also referred to as app marketplace).

A consumer device is an electronic device that interacts with a mobile device, and it may be a mobile device too. Additionally, the consumer device may be a workstation, a set-top box, an Internet-enabled household appliance, a smart speaker (e.g., Amazon Echo, Google Home).

Operating Environment

A beauty artist is an artist whose medium is the human body, and who applies one or more style such as makeup and hair style to a consumer. The applied style may include fashion makeup, theatrical makeup, special make-up effects, bridal makeup, airbrushing, and hair style including hair color. The consumer (also referred to as client) may be another human.

The offline interaction between a beauty artist and a consumer is often inefficient. With the prevalence of mobile devices, it is desirable for a beauty artist to manage the artist's interaction with a consumer through a mobile application. We refer such mobile application as a styling platform for a beauty artist to manage all interactions with a consumer, except the actual application of a styling feature (also referred to as a "look") on the consumer. The styling platform is also referred to as a beauty application, and the two terms are used interchangeably.

FIG. 1 illustrates the operating environment of a styling platform in a mobile device per one embodiment of the invention. A beauty artist uses an artist's mobile device 102, and a consumer uses a consumer device 104. The artist's mobile device 102 and the consumer device 104 communicate with each other through a communication network 190, and both communicate with one or more cloud servers 150.

The artist's mobile device 102 contains a styling platform 112, which is a mobile application (referred to as app 1) that is also referred to as a beauty application, through which the beauty artist may interact with consumers. The consumer device 104 contains a styling agent 114 (referred to as app 2), which is another mobile application through which the consumer may interact with the beauty artist. The styling platform 112 and the styling agent 114 may be provided by the same vendor that is independent from the manufacturer of the artist's mobile device 102 and the consumer device 104. In one embodiment, the styling platform 112 and the styling agent 114 may be the same mobile application, but different functions are used when the mobile application serves as the styling platform 112 and the styling agent 114.

The cloud servers 150 provide computing and storage resources for the artist's mobile device 102 and the consumer device 104. The cloud servers 150 may be owned and operated by a third party (e.g., a cloud provider/operator such as Amazon.com®, Microsoft®, Google®, CenturyLink®, Rackspace®, or Computer Sciences Corporation (CSC®)). The third party may be independent from the vendor of the styling platform 112 and styling agent 114 and the manufacturer of the artist's mobile device 102 and the consumer device 104.

The communication network 190 may be a variety of wireline or wireless networks. The wireline network may deploy technologies such as the universal asynchronous receiver/transmitter (UART) technology, the controller area network (CAN) technology, and the inter-integrated circuit (I2C) technology; and the wireless communication network may deploy technologies such as wireless local area network (WLAN) (e.g., WiFi™), Bluetooth, cellular the third/fourth/fifth generation (3G/4G/5G). The communication network 190 uses a set of communication links for communication among the artist's mobile device 102, the consumer device 104, and the cloud servers 150.

While FIG. 1 illustrates that the styling platform 112 is within a mobile device 102, in some embodiments, the styling platform 112 may be implemented in a stationary computing device such as desktop computer or computer server. The styling platform 112 may also be implemented at a website for the consumer to log in using a browser and interact with the beauty artist.

Operations Relating to Styling Platform

Figure 2:
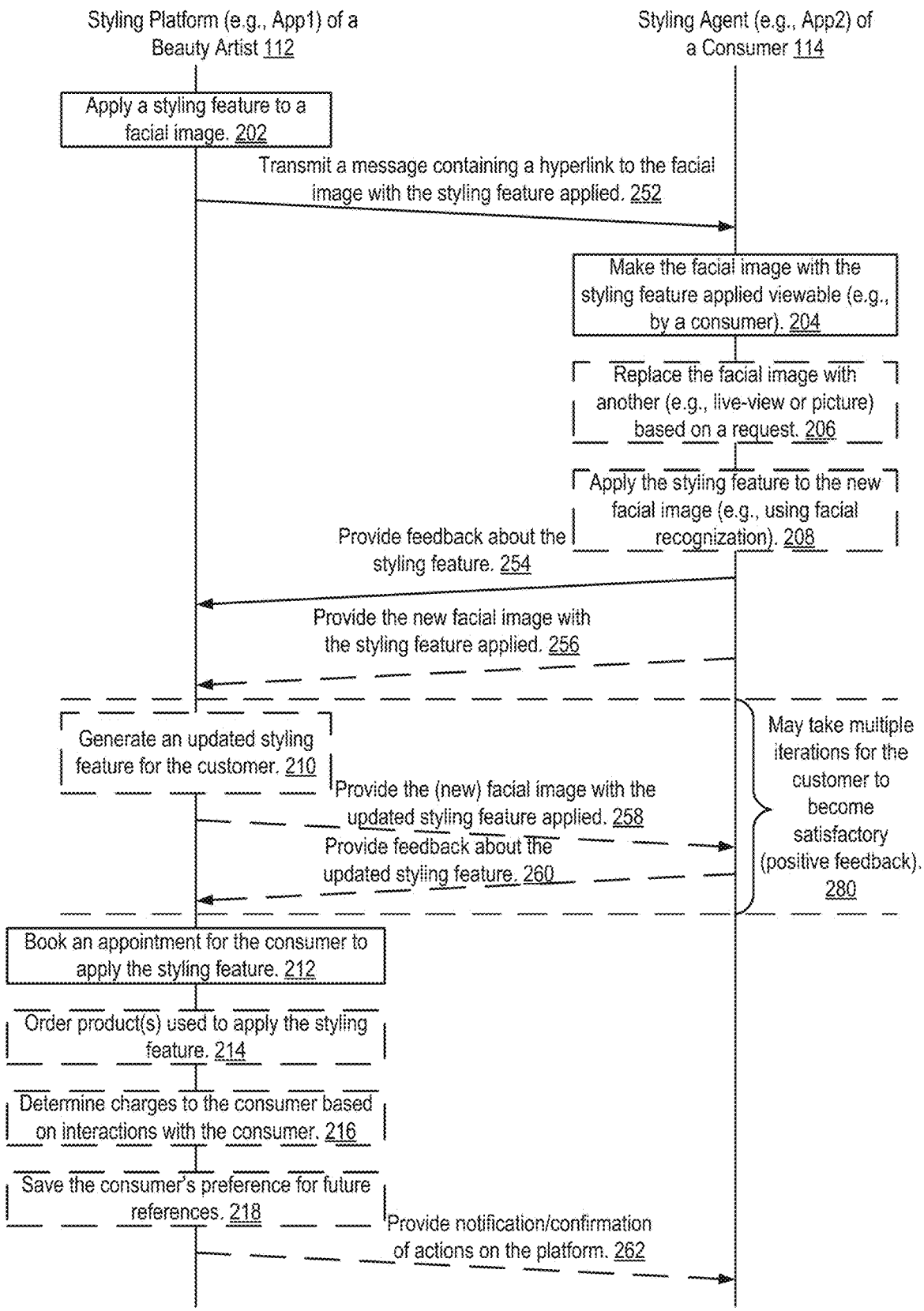
FIG. 2 illustrates operations relating to a styling platform per one embodiment of the invention.

FIG. 2 illustrates operations relating to a styling platform per one embodiment of the invention. The illustrated operations are between the styling platform 112 and the styling agent 114, and both may interact with the cloud servers 150.

At reference 202, the styling platform 112 may apply a styling feature to facial image based on the beauty artist's input. The application of the styling feature may include one or more of: (1) applying makeups such as eyeliner, eye shadow, blush, lipstick, and foundation; (2) enhancing facial features such as slimming a face, lifting cheeks, enhancing a nose, whitening teeth, and removing blemishes, oily shine, bags under the eyes, and dark circles around the eyes; (3) changing hair styles including hair colors, and (4) applying accessories (e.g., glasses, hat, scarf), jewelry, and clothing. While one styling feature is discussed, more styling features may be applied by the styling platform 112 at reference 202.

The application of the styling feature may include automatically (without user input) identifying outlines of facial features, points of the facial features ("facial feature points"), age, gender, and race of a person from the person's face. The identified facial features may include mouth, eyes, eye brows, nose, irises, pupils, teeth, lips, cheeks, hairs, and T-zone (an area including the nose and across the forehead). A facial analyzer may perform the facial feature identification, and the facial analyzer may be a part of the styling platform 112. The facial analyzer may perform the facial feature identification using the styling platform 112 alone, or with the help of the cloud servers 150.

Figures 4, 5:
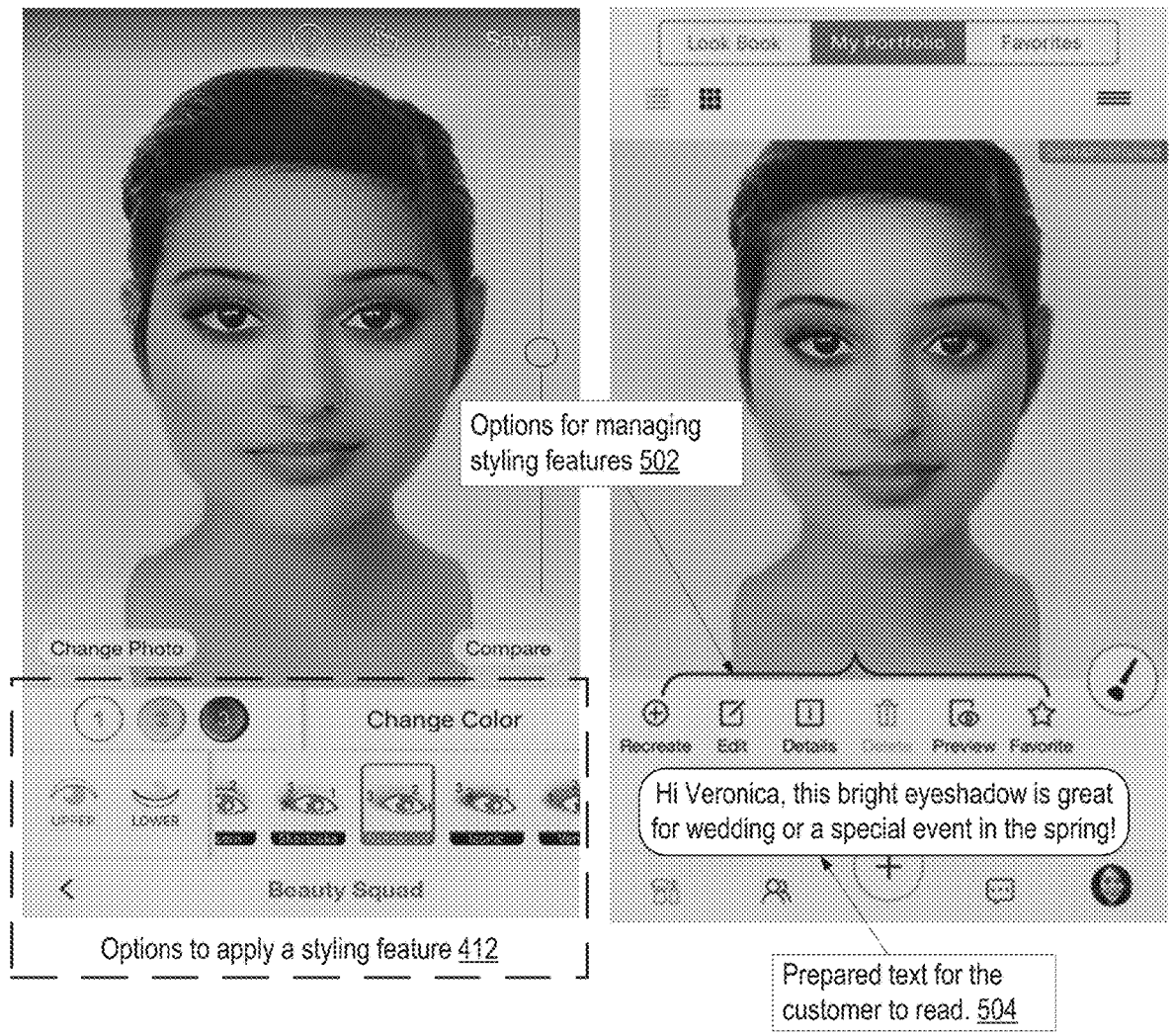
FIG. 4 illustrates a user interface within a styling platform for a beauty artist to apply one or more styling features to a facial image per one embodiment of the invention.
FIG. 5 illustrates a user interface within a styling platform for a beauty artist to edit a facial image per one embodiment of the invention.

FIG. 4 illustrates a user interface within a styling platform for a makeup artist to apply one or more styling features to a facial image per one embodiment of the invention. The styling platform may provide options to apply styling feature at reference 412. The styling platform may also identify facial features (e.g., the eyes) within the facial image and the makeup artist may apply one of the options (e.g., eyeshadow color selection) to the eyes. The options may be applied to the upper or lower portion of the eyelids based on the makeup artist's selection, and the artist may select from various shapes of the eyeshadow. The user interface may also include options to apply to other styling features discussed above relating to reference 202.

The facial image may be a stock image (e.g., provided by the styling platform) or an image of the consumer that the makeup artist plans to serve. Additionally, the facial image may be captured live by a camera of the mobile device 102. The styling platform provides an option to switch the facial image using "change photo" option on the user interface. The styling platform also provides an option to compare images using "Compare," through which the beauty artist may compare the facial image before and after the styling feature applied.

The application of one or more styling features may also require editing options to help a makeup artist to present the one or more styling features to a consumer. FIG. 5 illustrates a user interface within a styling platform for a makeup artist to edit a facial image per one embodiment of the invention. The options for managing styling features 502 include recreating/editing/deleting/previewing a styling feature, and also providing details of a styling feature or saving a styling feature as favorite. The makeup artist may also write a note for the consumer to read when the consumer sees one or more styling features applied to the facial image. The prepared text for the consumer to see at reference 504 is shown in the figure. Once the makeup artist finishes the work, the one or more styling features are applied to the facial image using the styling platform. The end result (the facial image with the one or more styling features applied) may be saved in the cloud servers 150, which provides a hyperlink to the saving location of the end result.

Referring back to FIG. 2, after the styling feature is applied to the facial image at reference 202, the styling platform 112 may transmit a message containing a hyperlink to the facial image with the styling feature applied at reference 252, based on the makeup artist's input. For example, the makeup artist may select the contact of the consumer from the styling platform 112, and clicking the contact in the styling platform 112 causes the message to be sent. The message may be a short message service (SMS) message (also known as text message), an email, or a message on another social network platforms such as Facebook, Twitter, Instagram, Pinterest, Wechat, Tumblr, Snapchat, etc. Note the message from the makeup artist to the consumer may not be the first message between the parties, and the consumer may send an earlier message to the makeup artist requesting the styling feature.

At reference 204, the styling agent 114 receives the message and makes the facial image with the styling feature applied viewable, e.g., by the consumer. The consumer may click the hyperlink included in the message, and the clicking causes the styling agent 114 reaches the saving location of the facial image with the styling feature applied. The consumer then may view the facial image with the styling feature applied through the styling agent 114. Additionally, the facial image with the styling feature may be viewed live by a camera of the consumer device 104. Once the consumer views the facial image with the styling feature applied, a communication session between the styling platform and the styling agent is established in one embodiment. The communication session may be established when the consumer launches the styling agent 114. The communication session is established because the beauty artist expects feedback from the consumer, and the two parties may exchange information through the communication session regarding the consumer's styling feature application.

The facial image may be a stock image in one embodiment, and the styling agent 114 may optionally replace the facial image with another based on a request from the consumer at reference 206. The replacement may be a live-view that the consumer captures using a camera of the consumer device 104. The replacement may be a picture that the consumer loads to the styling agent 114. After the facial image is updated with the replacement (the new) image, the styling feature provided by the styling platform 112 can be applied to the replacement image at reference 208. The styling agent 114 may use the facial analyzer discussed above relating to reference 202 to recognize facial features and thus apply the styling feature on the replacement image.

Figure 6:
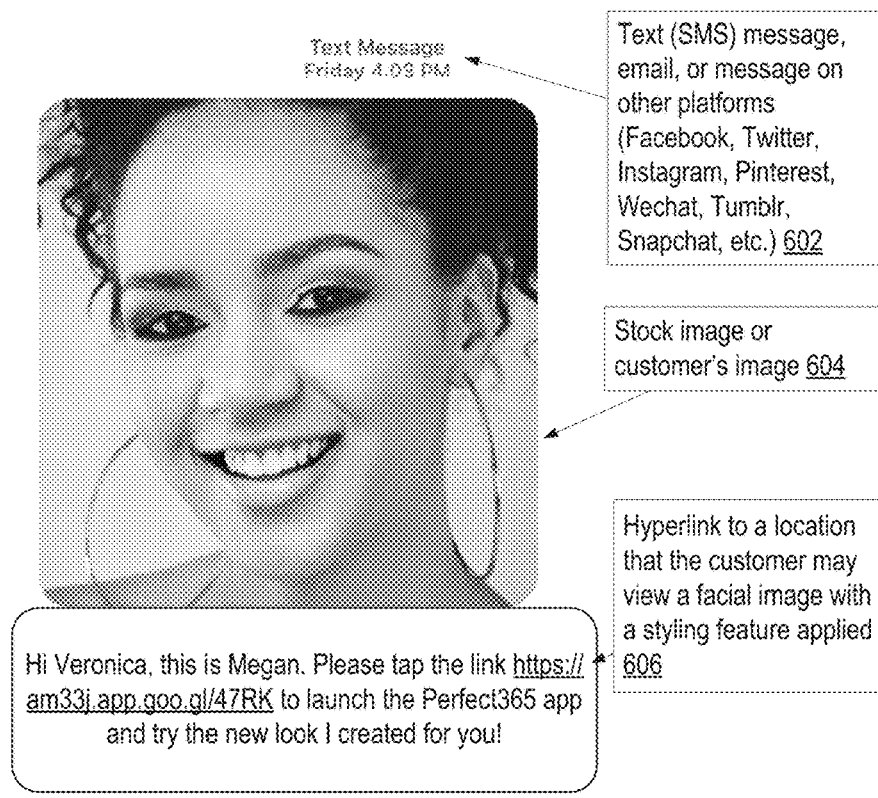
FIG. 6 illustrates a message sent from a beauty artist to a consumer per one embodiment of the invention.

FIG. 6 illustrates a message sent from an artist to a consumer per one embodiment of the invention. The message, as indicted by reference 602, may be a text message, an email, or a message on another social network platforms such as Facebook, Twitter, Instagram, Pinterest, Wechat, Tumblr, Snapchat, etc. The message may include a stock image or the consumer's image as illustrated at reference 604. The message also includes a hyperlink to a location such as the uniform resource locator (URL) (regular or shorten) as illustrated at reference 606.

By following the hyperlink (e.g., through the consumer's tapping/clicking), a styling agent may be launched when the consumer is registered and have the application on the consumer device. Otherwise, the consumer is reminded of and provided guidance for downloading the application and registering, so that after the downloading and registration, the styling agent will be launched.

Figure 7:
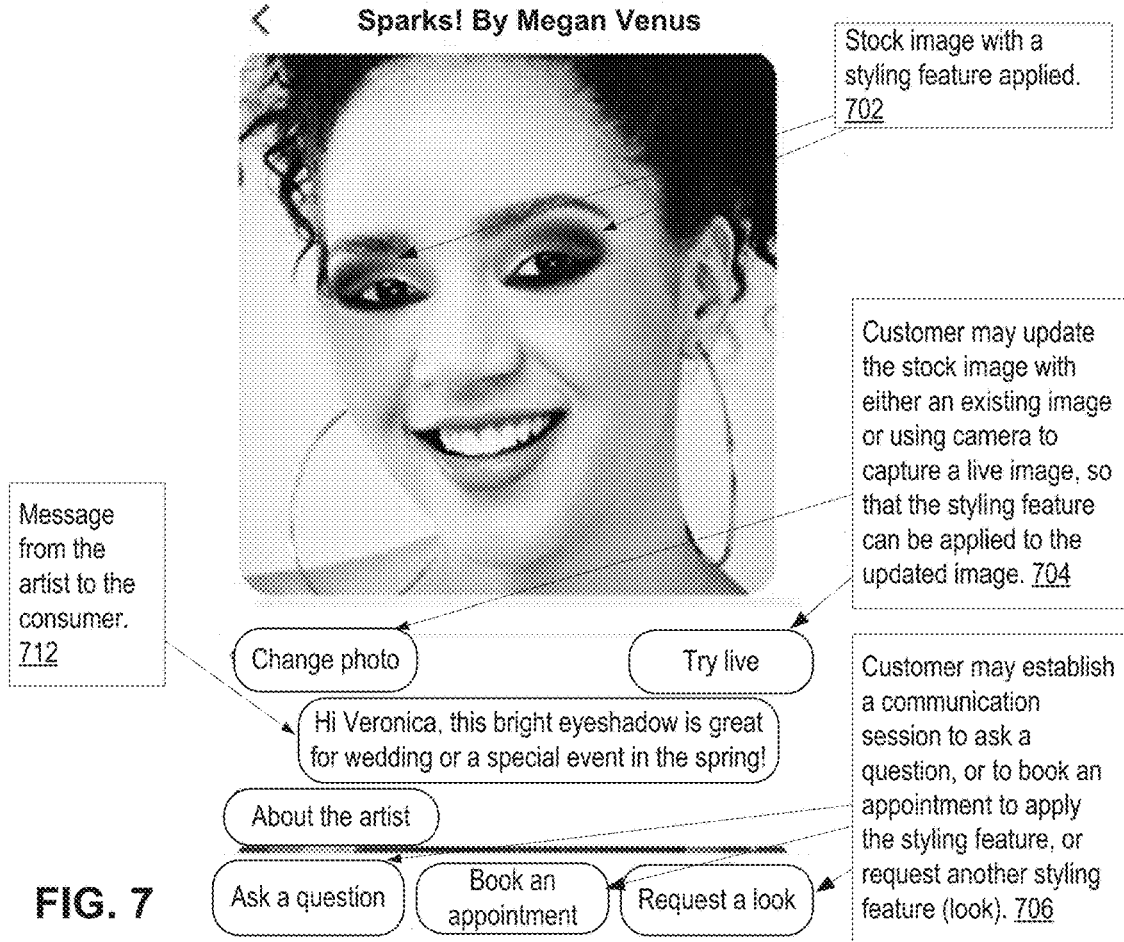
FIG. 7 illustrates a user interface within a styling agent for a consumer to interact with a beauty artist about applying one or more styling features per one embodiment of the invention.

FIG. 7 illustrates a user interface within a styling agent for a consumer to interact with a beauty artist about applying one or more styling features per one embodiment of the invention. The styling agent may be the styling agent 114. The user interface within the styling agent 114 may be displayed on the consumer device 104 once the styling agent 114 is launched after the consumer receives the message from the artist at reference 252.

At reference 702, the styling agent 114 displays the stock image with a styling feature applied. The consumer may choose to update the stock image with either an existing image by selecting "Change photo" or use a camera to capture a live image by selecting "Try live" at reference 704.

Once the image is updated, the styling agent 114 will apply the same styling feature that the artist applies to the updated image. In other words, the styling agent 114 may not alter the styling feature (but may alter the facial image) in this embodiment. The user interface may also include the text that the artist created (see reference 504) for the consumer about the styling feature at reference 712.

After viewing the facial image (provided by the artist or updated by the consumer) with the styling feature applied, the consumer may establish a communication session at reference 706. At reference 706, the consumer may ask a question regarding the styling feature, book an appointment to apply the styling feature, or request another styling feature (also referred to as "look") from the artist. The communication session may be created once the consumer responds. For example, the communication session may be created when the consumer opens the hyperlink that the artist sent over and/or launches the styling agent.

Note that while FIG. 7 illustrates a communication session within the beauty application itself, the communication session may be established in a different platform. For example, the communication session may be through short message service (SMS) messages (also known as text messages), emails, or messages on another social network platforms such as Facebook, Twitter, Instagram, Pinterest, Wechat, Tumblr, Snapchat, etc. Furthermore, the communication may be through an offline channel such as scanning one or more barcodes or Quick Response (QR) codes, or even letter.

Referring back to FIG. 2, the styling agent 114 provides feedback about the styling feature at reference 254. The feedback may include asking a question regarding the styling feature. The styling agent 114 may optionally provide the new facial image (e.g., the consumer's own image instead of the stock image provided by the artist) with the styling feature applied at reference 256.

At reference 210, based on the feedback from the consumer, the beauty artist may generate and apply an updated styling feature for the consumer using the styling platform 112, similar to the operations discussed above relating to reference 202. The styling platform 112 provides the (new, when the consumer alters the facial image) facial image with the updated styling feature applied at reference 258. The styling agent 114 may optionally provide feedback about the updated styling feature at reference 260. As noted at reference 280, it may take multiple iterations for the consumer to become satisfactory, and indicate so in the consumer's feedback.

Once the consumer is satisfied with the styling feature (after one or more iterations of styling feature application by the beauty artist, the styling platform 112 may book an appointment for the consumer to apply the styling feature at reference 212. The styling platform 112 may examine availability of the beauty artist through checking the availability of the beauty artist. For example, the styling platform 112 may integrate a calendar application of the artist's mobile device 102 within the styling platform 112. Based on the consumer's availability provided by the consumer through a message from the styling agent 114 to the styling platform 112, the styling platform 112 books an appointment for the consumer, and lists the appointment in the artist's calendar application. and notifies the consumer of the appointment.

With the styling feature being applied on the facial image digitally (one or multiple times) through the styling platform 112, the consumer and the beauty artist may reach an agreement on the digitally applied styling feature. Thus, it is more likely the consumer will be satisfied when the beauty artist applies the styling feature physically on the face or hair of the consumer. Also, digitally applying the styling feature on the facial image is much easier to remove and revise than physically applying the styling feature on the consumer's face or hair. Digitally applying the styling feature through the styling platform 112 also does not use real makeup products thus saves money for the beauty artist and consumer since the consumer typically pays for each trial makeup session when the styling feature is applied physically on the consumer. Thus, the beauty artist and the consumer reaching an agreement on the digitally applied styling feature first before applying the styling feature physically on the consumer's face likely results in a better user experience and less expenditure by the beauty artist and the consumer.

At reference 214, the styling platform 112 optionally identifies and orders one or more products used to apply the styling feature from a distributor (e.g., a wholesaler or retailer) of the one or more products. In one embodiment, the beauty artist places the order; and in an alternative embodiment, the styling platform 112 automatically places the order without the beauty artist's involvement. Beauty products are used to enhance or alter the appearance of a body, and most beauty products are designed to apply to face or hair. Common beauty products include lipstick, mascara, eye shadow, foundation, rouge, skin cleanser, and skin lotion.

At reference 216, the styling platform 112 determines the charges to the consumer based on the interactions with the consumer. The styling platform 112 logs information regarding interactions with the consumer, the beauty artist may retrieve the information from the styling platform 112 and determine how much to charge the consumer. The information regarding interactions with the consumer may include the number of iterations the beauty artist applying styling features digitally, the number of times the beauty artist responding to the consumer, the length of duration from the first styling feature application to the agreed-upon styling feature application, and other factors that the platform may set. The beauty artist may add further factors for charging the consumer. For example, the beauty artist may offer some services for free (e.g., free first styling feature when appointment is booked by a certain time); the beauty artist may offer one time fix fee payment regardless of how many styling feature a consumer tries; the beauty artist may allow a consumer to try some products for certain styling feature first before buy; and the beauty artist may offer subscription services to a consumer so that the consumer may get some styling features applied by a fixed fee for a duration (e.g., monthly subscription).

At reference 218, the styling platform 112 may optionally save the consumer's preference on styling features for future reference. The preference may be based solely on the digitally applied styling feature in one embodiment, and alternatively the preference may be based on both digitally applied styling feature and physically applied styling feature after the consumer applies the styling feature on the consumer's face. The preference of the consumer may be in the form of a visual note in one embodiment.

At reference 262, the styling platform 112 optionally provides notification and confirmation of actions on the styling platform 112 to the styling agent 114, so that the consumer is aware of the action. For example, the styling platform 112 may notify the styling agent 114 that an appointment has been booked for applying the styling feature physically on the consumer's face by the beauty artist. The styling platform 112 may also notify the styling agent 114 that a product has been ordered, or a charge has been or will be posted for the interactions with the consumer.

Figure 8:
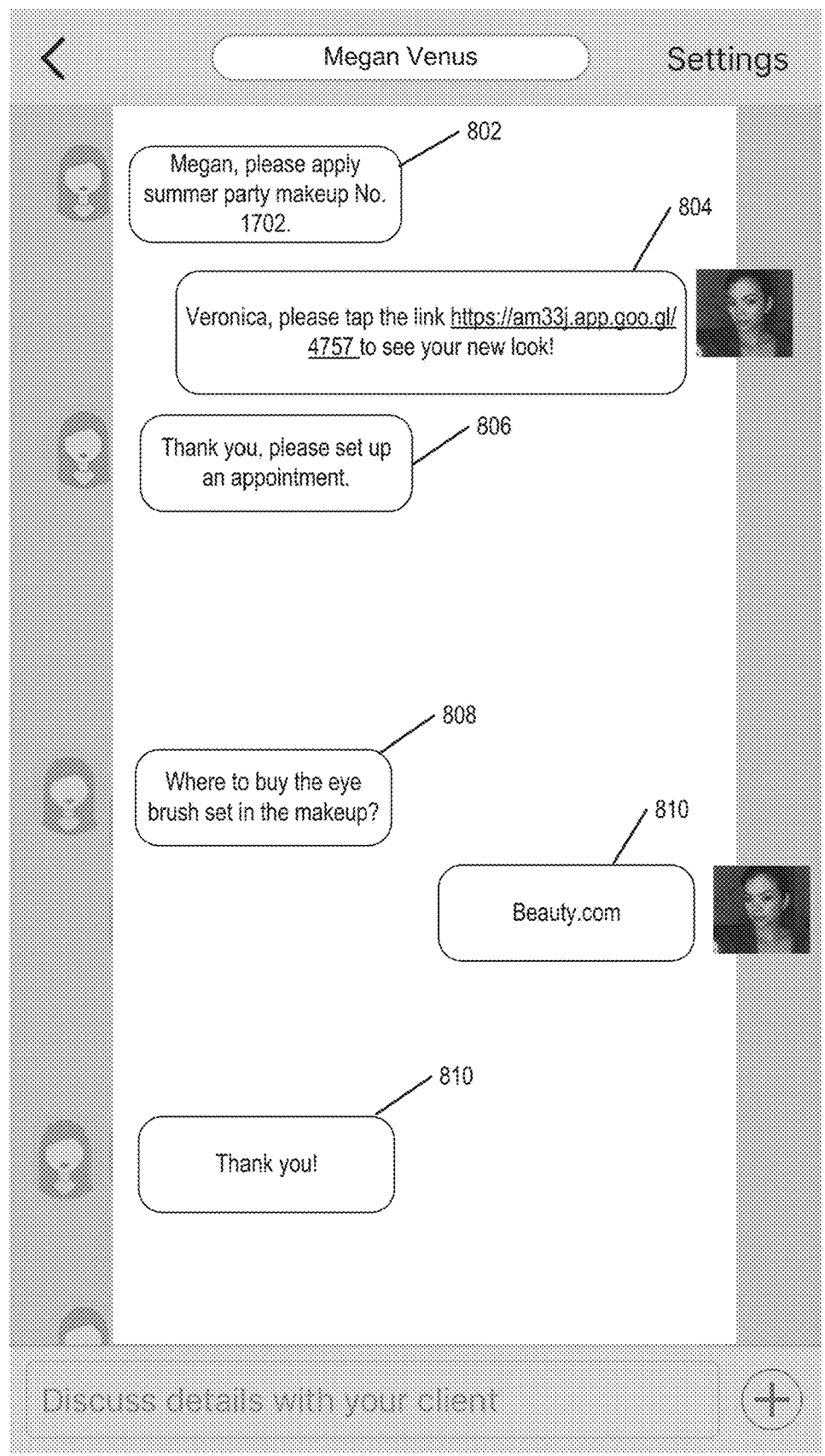
FIG. 8 illustrates an interaction between a beauty artist and a consumer in a communication session per one embodiment of the invention.

FIG. 8 illustrates an interaction between a beauty artist (Megan Venus) and a consumer (Veronica Diaz) in a communication session per one embodiment of the invention. In this example, the consumer messages the artist first, asking for apply a styling feature, "summer party makeup No. 1702" at reference 802. Based on the request, the beauty artist replies with a message at reference 804 with a hyperlink to the digitally applied styling feature (summer party makeup No. 1702) to a facial image. The consumer reviews the styling feature and agrees to apply the styling feature physically on her by requesting an appointment at reference 806. In this interaction, the consumer requires no revision of the styling feature. Yet the consumer may request one or more revisions of the styling feature in another embodiment as illustrated at FIG. 2 (e.g., reference 280).

Later on during the communication session, the consumer asks for the product used for the styling feature at reference 808, the beauty artist makes recommendation of a vendor at reference 810, and the consumer acknowledges the recommendation at reference 810. Note that the consumer does not make the purchase from the beauty artist. Yet the styling platform logs the interactions between the consumer and the beauty artist, and the beauty artist may present the interaction with the consumer to the recommended vendor for commission.

Figure 9:
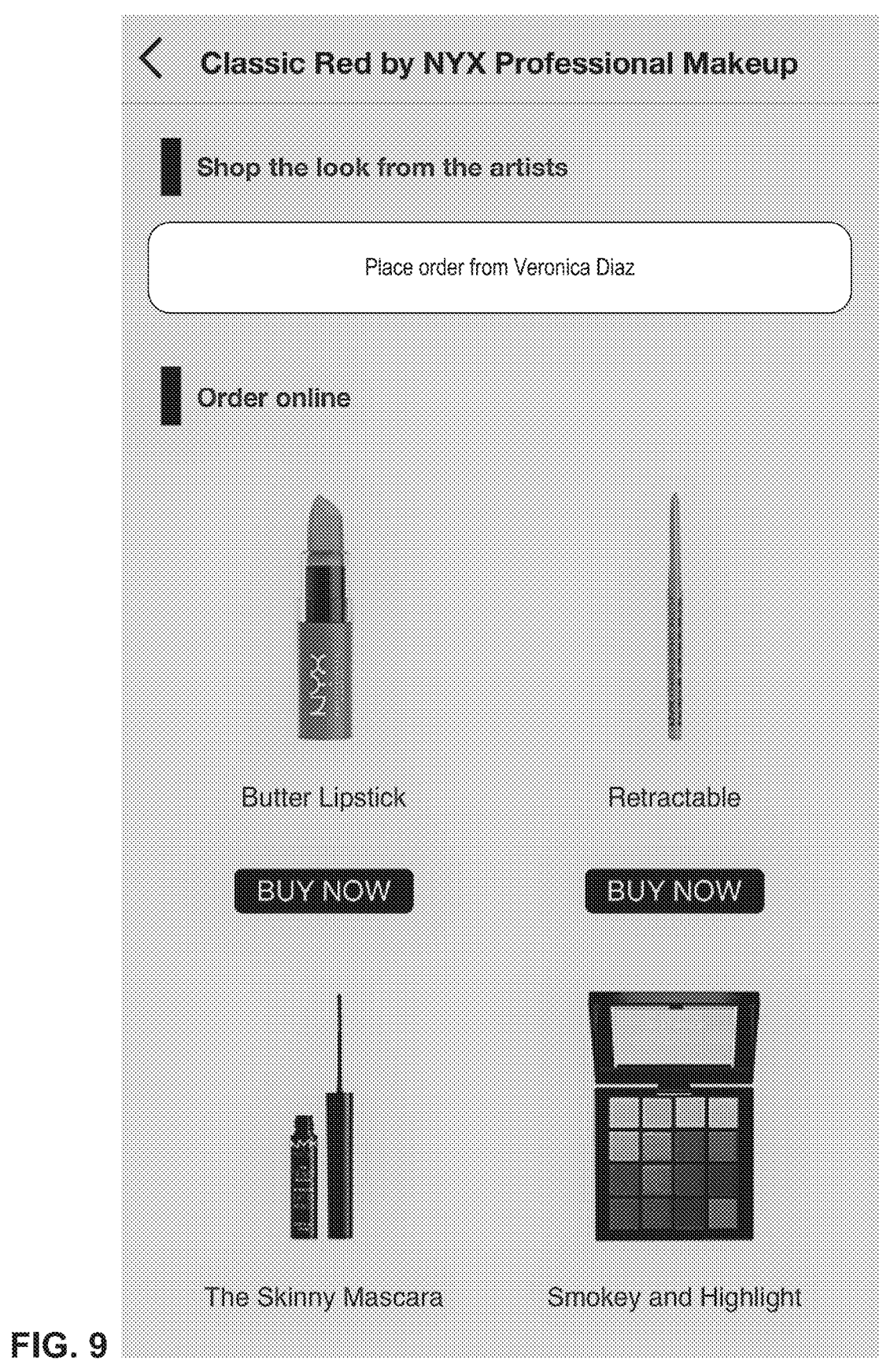
Figure 10:
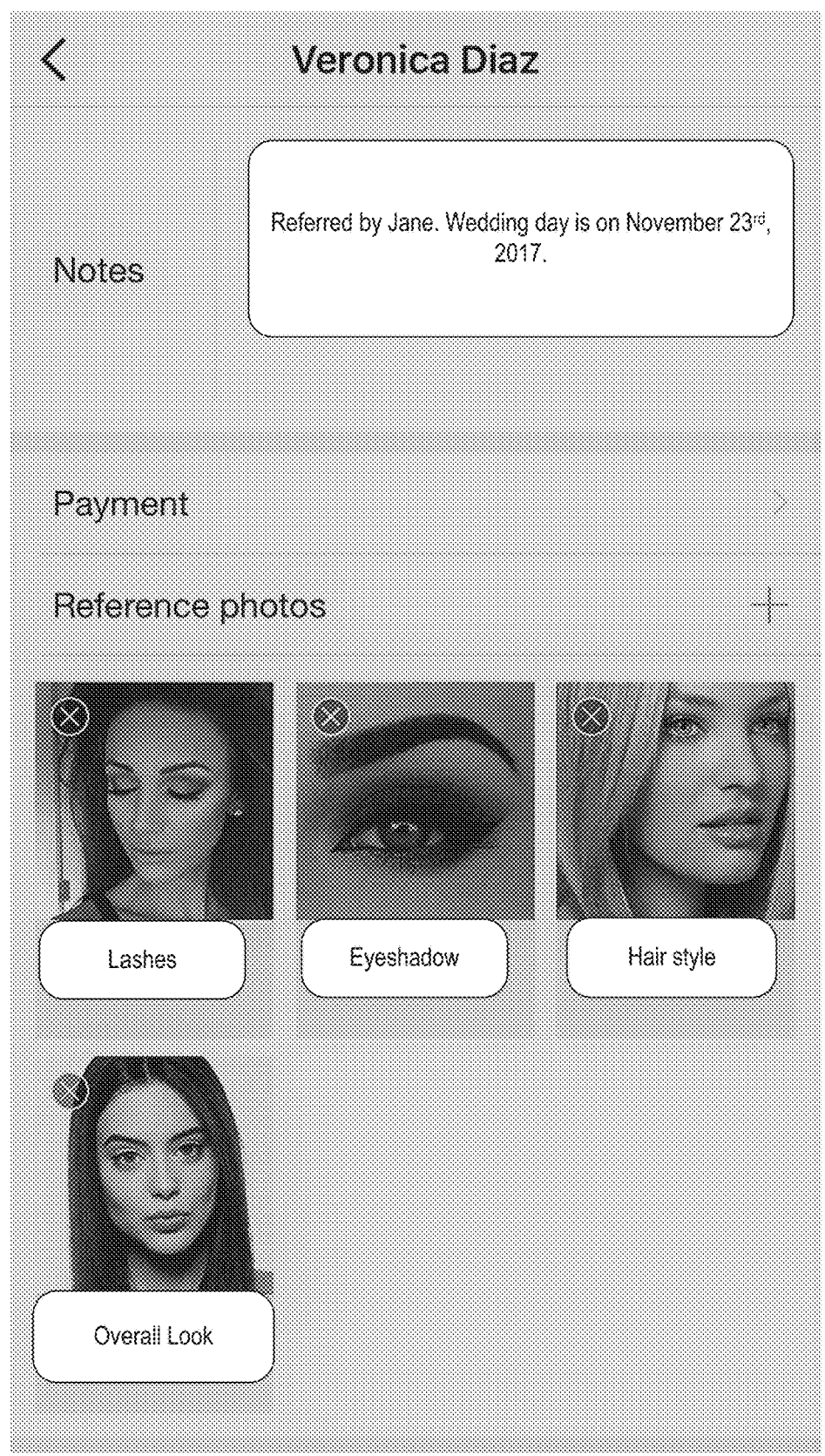
FIG. 10 illustrates a visual note for a consumer in a styling platform per one embodiment of the invention.

FIG. 9 illustrates making a purchase through a styling platform per one embodiment of the invention. The listed products are for a consumer (Veronica Diaz). The styling platform may generate the list from the styling feature (e g, summer party makeup No. 1702) that a beauty artist (Megan Venus) created for the consumer. The beauty artist may place an order for the products on behalf of the consumer through the styling platform in one embodiment. The vendor that receives the order may offer commission to the beauty artist for such purchase. Note that in one embodiment, a styling agent may also have a product purchase selection user interface, from which a consumer may select the product(s) to buy from the beauty artist FIG. 10 illustrates a visual note for a consumer in a styling platform per one embodiment of the invention. The visual note records the consumer's preference. The visual note includes the name of the consumer (Veronica Diaz), and comments about the consumer (in this case, who is the referral and for service of what event). The visual note also includes payment information from the consumer. The visual note additionally includes the consumer preference in the "Reference photos" section, where the styling platform records the preference of the consumer, including lashes, eyeshadow, hairstyle, and overall look. The visual note may include other information that the beauty artist generates while working with the consumer.

Figure 3:
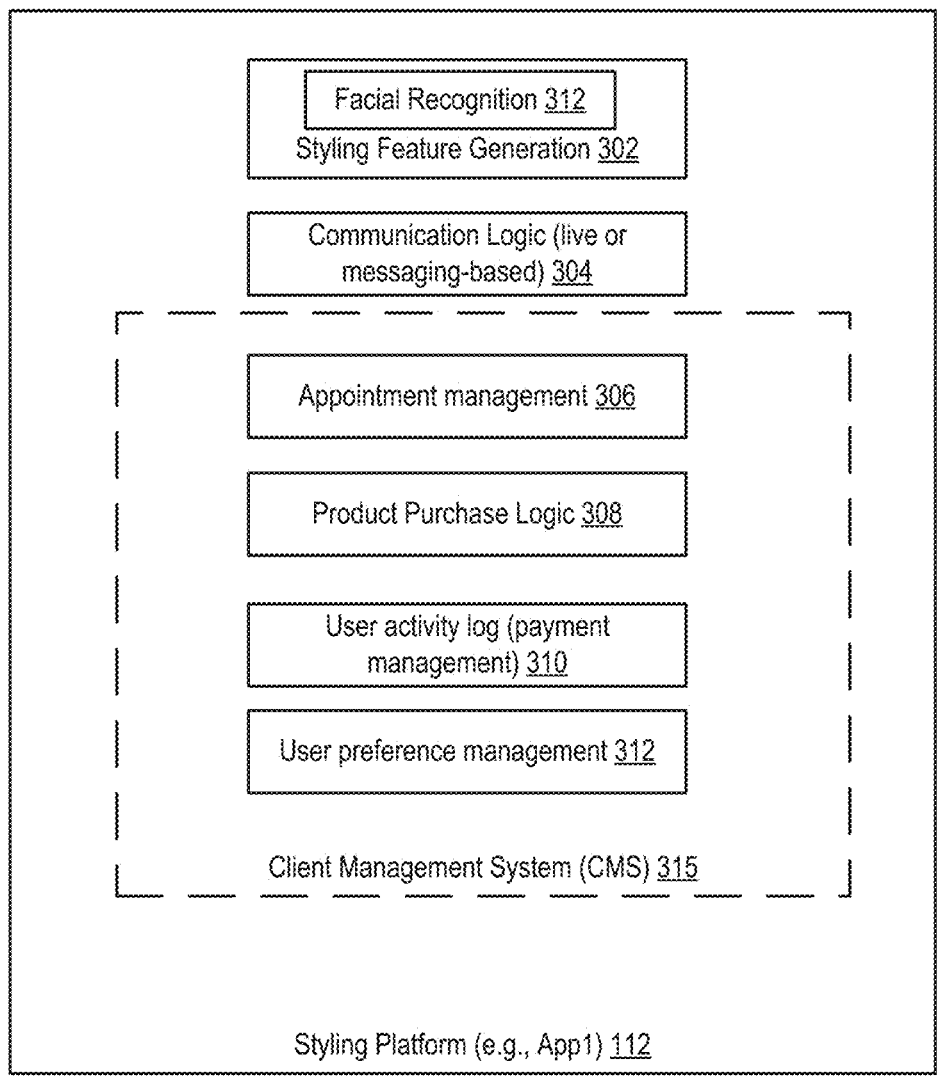
FIG. 3 illustrates a number of functional blocks of a styling platform per one embodiment of the invention.

Referring back to FIG. 3, which illustrates a number of functional blocks of a styling platform per one embodiment of the invention. The styling platform is the styling platform 112 discussed above. The styling platform 112 may include a styling feature generation block 302. The styling feature generation block applies a styling feature to a facial image, thus perform operations discussed above relating to reference 202. The styling feature generation block may include a facial recognition module that perform the function of facial recognition such as the facial analyzer discussed above.

The styling platform 112 may include a communication logic 304, which is to establish a communication session between the styling platform and a styling agent so that a beauty artist using the styling platform and a consumer using the styling agent may communicate with each other though the communication session. The communication session may be text based, or video stream based. In the video stream based communication session, the beauty artist may generate a styling feature live for the consumer in the communication session. For example, the consumer may provide a snapshot using the camera of the consumer device. The "live" image of the consumer is transmitted to the artist. The beauty artist then identifies the facial features from the live image, applies the styling feature to the live image, and shows the live image with the styling feature applied, all in the communication session. The live stream of the communication session offers quick feedback to both the beauty artist and the consumer, and may be considered desirable. In some embodiments, the communication session may also include one or more of a live audio stream between the beauty artist and the consumer, audio messages sent by the beauty artist and/or the consumer, and/or video messages sent by the beauty artist and/or the consumer.

The styling platform 112 may also include a client management system (CMS) 315. The client management system 315 may include (1) an appointment management module 306 that may perform operations discussed above relating to reference 212; (2) a product purchase logic 308 that may perform operations discussed above relating to reference 214; (3) a user activity log module 310, which may also manage consumer's payment, and which performs operations discussed above relating to reference 216; and (4) user preference management module 312 that may perform operations discussed above relating to reference 218. Note one or more of these modules/logics may be implemented outside of the CMS 315 in some embodiments.

Flow Diagram

The operations in the flow diagram will be described with reference to the exemplary embodiments of the other figures. However, the operations of the flow diagram can be performed by embodiments of the invention other than those discussed with reference to the other figures, and the embodiments of the invention discussed with reference to these other figures can perform operations different than those discussed with reference to the flow diagram.

Figure 11:
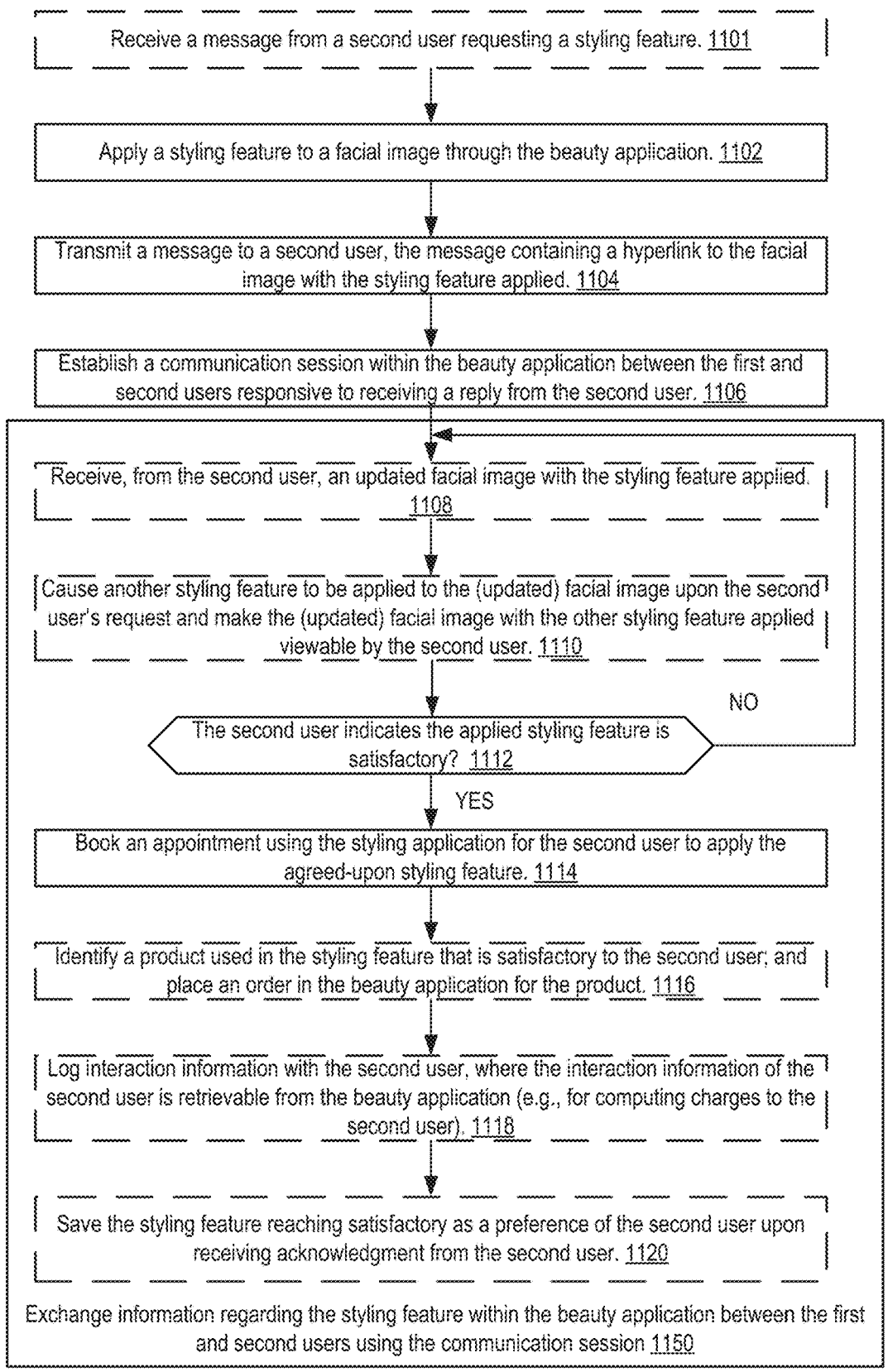
FIG. 11 is a flow diagram illustrating operations of a styling platform per one embodiment of the invention.

FIG. 11 is a flow diagram illustrating operations of a styling platform per one embodiment of the invention. Method 1100 may be performed by a beauty application such as the styling platform 112 in one embodiment. The beauty application is a mobile application implemented in a mobile device such as the artist's mobile device 102. A beauty artist interacts with the beauty artist's consumer through the beauty application, and a consumer interacts with the beauty artist through a styling agent such as styling agent 114 contained in a consumer device 104 in one embodiment. The beauty artist is referred to as the first user and the consumer the second user in method 1100.

At reference 1101, the beauty application optionally receives a message from the second user requesting a styling feature. The message may indicate the styling feature the second user requires. The message may also include a facial image of the second user. The facial image may be captured live using a camera of the consumer device.

At reference 1102, a styling feature is applied to a facial image through the beauty application. The facial image may be the one received from the second user, and the facial image may also be a stock image. The styling feature is applied based on the first user using beauty application as discussed relating to FIGS. 4-5.

At reference 1104, a message is transmitted from the first user to the second user through the beauty application, and the message containing a hyperlink to the facial image with the styling feature applied. The operations are discussed relating to FIG. 2 reference 252.

At reference 1104, a communication session is established within the beauty application between the first and second users responsive to receiving a reply from the second user. The reply is the second user's view of the facial image with the styling feature applied in one embodiment. The styling agent sends the beauty application the reply once the second user launches the styling agent in one embodiment.

At reference 1150, information regarding the styling feature is exchanged within the beauty application between the first and second user using the communication session. The second user may decide not to apply the styling feature physically on the second user (e.g., the face or hair), and tell the first user as such using the communication session (e.g., a message sent from the styling agent to the beauty application). In that case the communication session may end. Alternatively, the second user may decide to pursue further, and may use the communication session to exchange information with the first user. The information exchange may include operations relating to 254-262 and/or 212-218.

In one embodiment, the operations of reference 1150 may include one or more of operations of references 1108-1120. Specifically, at reference 1108, the beauty application may receive from the second user (through the styling agent) an updated facial image with the styling feature applied. The second user may switch the facial image provided by the first user with the updated facial image, but the same styling feature from the first user is applied to the updated facial image. The operations at reference 1108 are explained above relating to references 204-208.

At reference 1110, the beauty application may cause another styling feature to be applied to the facial image or the updated facial image upon the second user's request, and make the facial image or the updated facial image with the other styling feature applied viewable by the second user. The second user's request may include detailed comments on what to change from the styling feature that the first user generated, and the first user may apply the other styling feature based on the detailed comments. The first user may present facial image or the updated facial image with the other styling feature applied to the second user, and the presentation may be similar to a message such as the one at reference 804.

The first user may also generate the styling feature live for the second user in the communication session. For example, the second user may provide a snapshot of the second user using the camera of the second user's consumer device. The "live" image of the second user is transmitted to the first user. The first user then identifies the facial features, applies the styling feature to the live image, and shows the live image with the styling feature applied, all in the communication session (without using a hyperlink to point to the image location somewhere). Such live update of styling feature may offer convenience to both the first and second users.

At reference 1112, the beauty application determines whether the second user indicates the applied styling feature is satisfactory. The applied styling feature may be the original styling feature applied at reference 1102, and it may also be the other styling feature applied at reference 1110. The second user may indicate the applied styling feature being satisfactory using a message transmitted from the styling agent to the beauty application.

If the second user is not satisfied with the applied styling feature at reference 1112, the flow goes back to reference 1108, and another styling feature may be applied and shown to the second user at reference 118 and 1110. The operations between 1108 and 1110 may iterate several times before the second user satisfies with the applied styling feature.

Once the second user is satisfied with the applied styling feature, the flow goes to reference 1114, and an appointment may be booked using the beauty application. Making appointment is discussed earlier relating to reference 212.

At reference 1116, a product used in the styling feature that is satisfactory to the second user is identified, and an order may be placed in the beauty application for the product. The ordering operations are discussed earlier relating to reference 214.

At reference 1118, the beauty application may log interaction information with the second user, where the interaction information of the second user is retrievable from the beauty application. The interaction information may be used to computing charges to the second user as discussed earlier relating to reference 216.

At reference 1120, the beauty application may save the styling feature reaching satisfactory as a preference of the second user. The saving of the styling feature is discussed earlier relating to reference 218.

Through method 1100, a beauty application is used as a single integrated platform for a beauty artist to manage styling feature application to the consumers of the beauty artist. The beauty artist may apply a styling feature on a facial image digitally using the beauty application. The beauty artist and a consumer may go through several iterations of applying one or more styling features to the consumer in a communication session within the beauty application until the consumer is satisfied. Thus, the consumer is more likely satisfied when the beauty artist applies the agreed-upon styling feature physical on the consumer's face or hair.

Additionally, the digitally applied a styling feature on a facial image is much easier to remove and revise than the physically applied the styling feature on the consumer's face or hair. Digitally applied styling feature does not use real makeup products thus saves money for the beauty artist.

Furthermore, the integrated platform for the beauty artist may allow the beauty artist to book an appointment for a consumer to apply a styling feature, to order a product to apply the styling feature, and to determine charge to the consumer based on the interactions of the consumer with the beauty artist, and to save the consumer's preference for future reference. The integrated platform thus offers efficiency and convenience to a beauty artist.

Mobile Device Implementing Embodiment of the Invention

Figure 12:
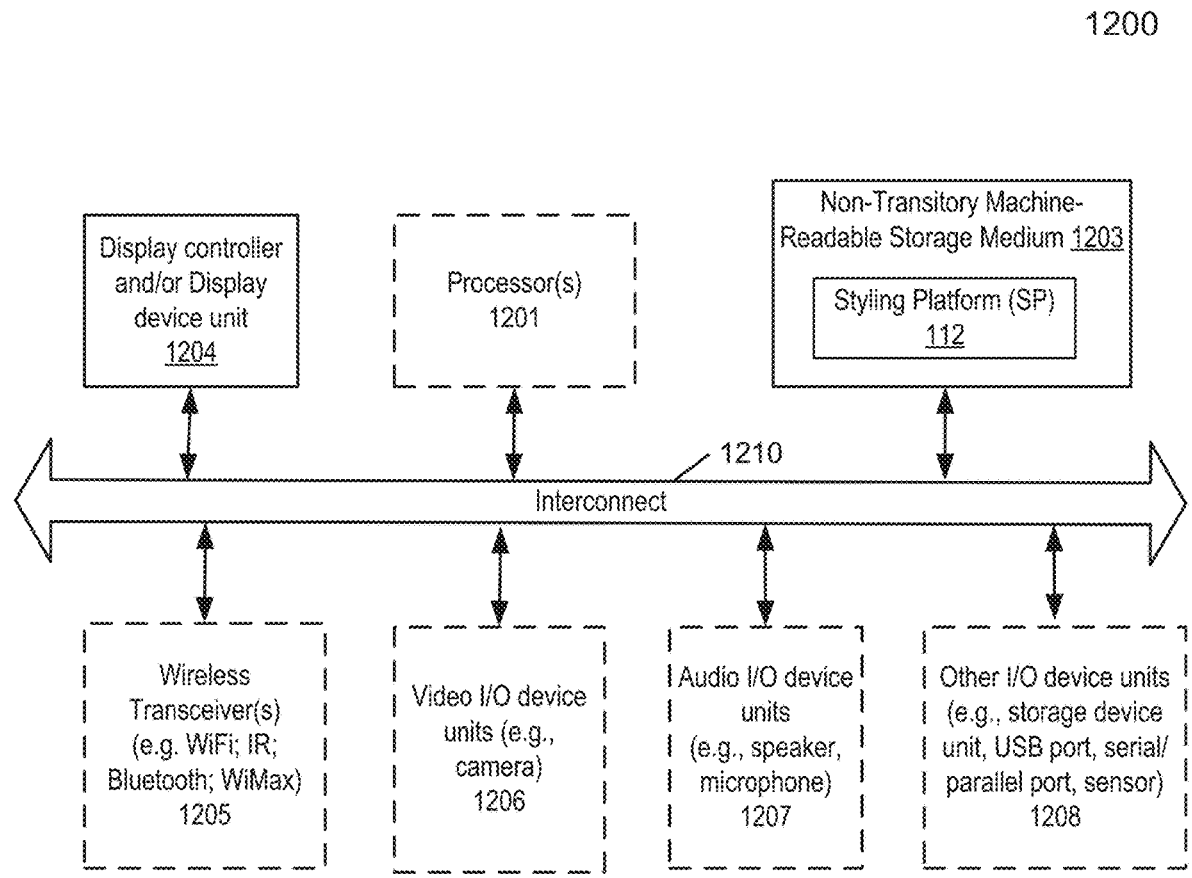
FIG. 12 is a block diagram illustrating a system that installs a styling platform per one embodiment of the invention.

FIG. 12 is a block diagram illustrating a system that may install a styling platform per one embodiment of the invention. The system 1200 may represent the mobile device 102 described above operations or methods described above. The system 1200 can include many different components. These components can be implemented as integrated circuits (ICs), portions thereof, discrete electronic devices, or other modules adapted to a circuit board such as a motherboard or add-in card of a computing system, or as components otherwise incorporated within a chassis of the computing system. Note also that the system 1200 is intended to show a high-level view of many components of the computing system. However, it is to be understood that additional components may be present in certain implementations and furthermore, different arrangement of the components shown may occur in other implementations.

In one embodiment, the system 1200 includes a processor 1201, non-transitory machine-readable storage medium 1203, and optionally device units 1204-1208 that are interconnected via a bus or an interconnect 1210. A processor 1201 may represent a single processor or multiple processors with a single processor core or multiple processor cores included therein. The processor 1201 may represent one or more general-purpose processors such as a microprocessor, a central processing unit (CPU), or processing device. More particularly, the processor 1201 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processor 1201 may also be one or more special-purpose processors such as an application specific integrated circuit (ASIC), a cellular or baseband processor, a field programmable gate array (FPGA), a digital signal processor (DSP), a network processor, a graphics processor, a network processor, a communications processor, a cryptographic processor, a co-processor, an embedded processor, or any other type of logic capable of processing instructions.

The processor 1201 may communicate with non-transitory machine-readable storage medium 1203, which in an embodiment can be implemented via multiple memory devices to provide for a given amount of system memory. The non-transitory machine-readable storage medium 1203 may include one or more volatile storage (or memory) devices such as random-access memory (RAM), dynamic RAM (DRAM), synchronous DRAM (SDRAM), static RAM (SRAM), or other types of storage devices. The non-transitory machine-readable storage medium 1203 may store information including sequences of instructions that are executed by the processor 1201, or any other device units. For example, executable code and/or data of a variety of operating systems, device drivers, firmware (e.g., input output basic system or BIOS), and/or applications can be loaded in the non-transitory machine-readable storage medium 1203 and executed by the processor 1201. An operating system can be any kind of operating systems, such as, for example, Windows® operating system from Microsoft®, Mac OS®/iOS® from Apple, Android® from Google®, Linux or other real-time or embedded operating systems such as VxWorks.

The non-transitory machine-readable storage medium 1203 contains the styling platform 112 discussed above, and the styling platform 112 may perform operations discussed above.

The system 1200 may optionally further include input/output (I/O) devices such as the device units 1204-1208, including display control and/or display device unit 1204, wireless transceiver(s) 1205, video I/O device unit(s) 1206, audio I/O device unit(s) 1207, and other I/O device units 1208 as illustrated. The wireless transceiver 1205 may be a WiFi transceiver, an infrared transceiver, a Bluetooth transceiver, a WiMax transceiver, a wireless cellular telephony transceiver, a satellite transceiver (e.g., a global positioning system (GPS) transceiver), or other radio frequency (RF) transceivers, or a combination thereof. The system 1200 may also include an ultrasound device unit (not shown) for transmitting a conference session code.

The video I/O device unit 1206 may include an imaging processing subsystem (e.g., a camera), which may include an optical sensor, such as a charged coupled device (CCD) or a complementary metal-oxide semiconductor (CMOS) optical sensor, utilized to facilitate camera functions, such as recording photographs and video clips and conferencing. An audio I/O device unit 1207 may include a speaker and/or a microphone to facilitate voice-enabled functions, such as voice recognition, voice replication, digital recording, and/or telephony functions. Other optional devices 1208 may include a storage device (e.g., a hard drive, a flash memory device), universal serial bus (USB) port(s), parallel port(s), serial port(s), a printer, a network interface, a bus bridge (e.g., a PCI-PCI bridge), sensor(s) (e.g., a motion sensor such as an accelerometer, gyroscope, a magnetometer, a light sensor, compass, a proximity sensor, etc.), or a combination thereof. The optional device units 1208 may further include certain sensors coupled to the interconnect 1210 via a sensor hub (not shown), while other devices such as a keyboard or thermal sensor may be controlled by an embedded controller (not shown), dependent upon the specific configuration or design of the system 1200.

Note that while the system 1200 is illustrated with various components, it is not intended to represent any particular architecture or manner of interconnecting the components; as such details are not germane to embodiments of the present invention. It will also be appreciated that an electronic device having fewer components or perhaps more components may also be used with embodiments of the invention.

Some portions of the preceding detailed descriptions have been presented in terms of algorithms and symbolic representations of operations on data bits within a computer memory. These algorithmic descriptions and representations are the ways used by those skilled in conferencing technology to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a conference device, or similar electronic computing device, that manipulates and transforms data represented as physical (electronic) quantities within the conference device's registers and memories into other data similarly represented as physical quantities within the conference device's memories or registers or other such information storage, transmission or display devices.

ENVIRONMENT UTILIZING EMBODIMENTS OF THE INVENTION

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A method implemented by a beauty application in a first mobile device of a first user, the method comprising:

applying a styling feature using input from the first user, through a user interface, to a facial image of a second user through the beauty application;

transmitting a message from the first mobile device of the first user to a second mobile device of the second user through the beauty application, the message containing a hyperlink to the facial image with the styling feature applied;

establishing a communication session within the beauty application between the first and second mobile devices responsive to receiving a reply from the second mobile device; and exchanging information regarding the styling feature within the beauty application between the first and second mobile devices using the communication session, wherein the facial image of the second user is updated, by a camera captured image of the second user using the second mobile device, and with the styling feature applied to the updated facial image, and wherein applying the styling feature to the updated facial image comprises using facial analysis to recognize facial features of the second user in the updated facial image.

2. The method of claim 1, wherein exchanging the information includes booking an appointment using the beauty application for the second user for styling feature application.

3. The method of claim 1, wherein exchanging the information includes, responsive to a request from the second user, updating the styling feature.

4. The method of claim 1, wherein exchanging the information includes, receiving from the second user, the updated facial image with the styling feature applied.

5. The method of claim 1, wherein exchanging the information includes saving the styling feature as a preference of the second user.

6. The method of claim 1, wherein exchanging the information includes logging information regarding interactions with the second user, wherein the interaction information of the second user is retrievable from the beauty application.

7. The method of claim 1, wherein exchanging the information includes:
identifying a product used in the styling feature; and
placing an order for the product through the beauty application.

8. The method of claim 1, wherein the message is a short message service (SMS) message, an email, or a message in a social network platform.

9. The method of claim 1, wherein activating the hyperlink causes the facial image with the styling feature applied viewable to the second user.

10. The method of claim 1, wherein during the communication session, the styling feature is updated, wherein the updated styling feature is viewable by the second user through the communication session.

11. A first mobile device of a first user, comprising:
a non-transitory machine-readable storage medium to store a beauty application; and
a processor coupled with the non-transitory machine-readable storage medium to process the stored beauty application, causing the first mobile device to:
apply a styling feature using input from the first user, through a user interface, to a facial image of a second user through the beauty application,
transmit a message from the first mobile device of the first user to a second mobile device of the second user through the beauty application, the message containing a hyperlink to the facial image with the styling feature applied,
establish a communication session within the beauty application between the first and second mobile devices responsive to receiving a reply from the second mobile device, and
exchange information regarding the styling feature within the beauty application between the first and second mobile devices using the communication session, wherein the facial image of the second user is updated, by a camera captured image of the second user using the second mobile device, and with the styling feature applied to the updated facial image, and wherein applying the styling feature to the updated facial image comprises using facial analysis to recognize facial features of the second user in the updated facial image.

12. The first mobile device of claim 11, wherein exchange of the information includes to book an appointment using the beauty application for the second user for styling feature application.

13. The first mobile device of claim 11, wherein exchange of the information includes to, responsive to a request from the second user, updating the styling feature.

14. The first mobile device of claim 11, wherein exchange of the information includes to, save the styling feature as a preference of the second user.

15. The first mobile device of claim 11, wherein the message is a short message service (SMS) message, an email, or a message in a social network platform.

16. A non-transitory machine-readable storage medium that provides a beauty application, which when executed by a processor of a first mobile device of a first user, cause the processor to perform operations comprising:
applying a styling feature using input from the first user, through a user interface, to a facial image of a second user through the beauty application;
transmitting a message from the first mobile device of the first user to a second mobile device of the second user through the beauty application, the message containing a hyperlink to the facial image with the styling feature applied;
establishing a communication session within the beauty application between the first and second mobile devices responsive to receiving a reply from the second mobile device; and
exchanging information regarding the styling feature within the beauty application between the first and second mobile devices using the communication session, wherein the facial image of the second user is updated, by a camera captured image of the second user using the second mobile device, and with the styling feature applied to the updated facial image, and wherein applying the styling feature to the updated facial image comprises using facial analysis to recognize facial features of the second user in the updated facial image.

17. The non-transitory machine-readable storage medium of claim 16, wherein exchanging the information includes booking an appointment using the beauty application for the second user for styling feature application.

18. The non-transitory machine-readable storage medium of claim 16, wherein exchanging the information includes, responsive to a request from the second user, updating the styling feature.

19. The non-transitory machine-readable storage medium of claim 16, wherein exchanging the information includes saving the styling feature as a preference of the second user.

20. The non-transitory machine-readable storage medium of claim 16, wherein exchanging the information includes logging information regarding interactions with the second user, wherein the interaction information of the second user is retrievable from the beauty application.

* * * * *